US012239956B2

(12) United States Patent
Kim et al.

(10) Patent No.: US 12,239,956 B2
(45) Date of Patent: Mar. 4, 2025

(54) PREPARATION METHOD OF SUPER ABSORBENT POLYMER COMPOSITION

(71) Applicant: LG CHEM, LTD., Seoul (KR)

(72) Inventors: Ki Hyun Kim, Daejeon (KR); Gicheul Kim, Daejeon (KR); Jinuk Choi, Daejeon (KR); Tae Yun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 780 days.

(21) Appl. No.: 17/611,321

(22) PCT Filed: Dec. 18, 2020

(86) PCT No.: PCT/KR2020/018642
§ 371 (c)(1),
(2) Date: Nov. 15, 2021

(87) PCT Pub. No.: WO2021/125871
PCT Pub. Date: Jun. 24, 2021

(65) Prior Publication Data
US 2022/0212166 A1 Jul. 7, 2022

(30) Foreign Application Priority Data

Dec. 20, 2019 (KR) .................. 10-2019-0172494
Jan. 20, 2020 (KR) .................. 10-2020-0007115
Nov. 6, 2020 (KR) .................. 10-2020-0148077
Dec. 15, 2020 (KR) .................. 10-2020-0175606

(51) Int. Cl.
B01J 20/26 (2006.01)
B01J 20/28 (2006.01)
B01J 20/30 (2006.01)
C08F 120/06 (2006.01)
C08F 122/10 (2006.01)
C08J 3/24 (2006.01)
C08K 5/098 (2006.01)

(52) U.S. Cl.
CPC .......... B01J 20/261 (2013.01); B01J 20/267 (2013.01); B01J 20/2803 (2013.01); B01J 20/3021 (2013.01); C08F 120/06 (2013.01); C08F 122/1006 (2020.02); C08J 3/245 (2013.01); C08K 5/098 (2013.01); B01J 2220/68 (2013.01)

(58) Field of Classification Search
CPC ........ B01J 20/26; B01J 20/261; B01J 20/267; B01J 20/2803; B01J 20/3021; B01J 2220/68; C08F 122/1006; C08F 120/06; C08J 3/245; C08K 5/098
USPC ...................................................... 502/402
See application file for complete search history.

(56) References Cited

U.S. PATENT DOCUMENTS

| 6,291,636 | B1 | 9/2001 | Miyake et al. |
| 7,163,966 | B2 | 1/2007 | Joy et al. |
| 2002/0193516 | A1 | 12/2002 | Bucevschi et al. |
| 2012/0035294 | A1 | 2/2012 | Kim et al. |
| 2012/0289607 | A1 | 11/2012 | Xiong et al. |
| 2013/0026412 | A1 | 1/2013 | Machida et al. |
| 2013/0039963 | A1 | 2/2013 | Lorant et al. |
| 2013/0264517 | A1 | 10/2013 | Matsumoto et al. |
| 2016/0311985 | A1 | 10/2016 | Jung et al. |
| 2016/0318002 | A1 | 11/2016 | Lee et al. |
| 2017/0233534 | A1 | 8/2017 | Kim et al. |
| 2018/0037686 | A1 | 2/2018 | Lee et al. |
| 2018/0185292 | A1 | 7/2018 | Rahmouni et al. |
| 2018/0298132 | A1 | 10/2018 | Yorino et al. |
| 2018/0318793 | A1 | 11/2018 | Yoon et al. |
| 2019/0329219 | A1 | 10/2019 | Watabe et al. |
| 2019/0329220 | A1 | 10/2019 | Watabe et al. |
| 2019/0338082 | A1 | 11/2019 | Iwamura et al. |
| 2019/0344242 | A1 | 11/2019 | Kim et al. |
| 2020/0155458 | A1 | 5/2020 | Wagner-Hattler et al. |
| 2020/0207929 | A1 | 7/2020 | Nam et al. |
| 2020/0270441 | A1 | 8/2020 | Lee et al. |
| 2021/0009725 | A1 | 1/2021 | Nam et al. |
| 2021/0147637 | A1 | 5/2021 | Matsumoto et al. |
| 2022/0193634 | A1 | 6/2022 | Min et al. |
| 2022/0212166 | A1 | 7/2022 | Kim et al. |

FOREIGN PATENT DOCUMENTS

| BR | PI1014798-5 A2 | 4/2016 |
| CN | 102471394 A | 5/2012 |
| CN | 102639229 A | 8/2012 |
| CN | 104667895 A | 6/2015 |
| CN | 105814088 A | 7/2016 |

(Continued)

OTHER PUBLICATIONS

Extended European Search Report issued from the European Patent Office dated Jul. 1, 2022 in connection with the corresponding European Patent Application No. 20902297.9.
Extended European Search Report issued from the European Patent Office dated May 27, 2022 in connection with the corresponding European Patent Application No. 20902298.7.
Extended European Search Report issued from the European Patent Office dated Mar. 10, 2022 in connection with the corresponding European Patent Application No. 20903021.2.
Office Action issued Jul. 27, 2023 for corresponding Chinese Patent Application No. 202080032716.3.

(Continued)

Primary Examiner — Edward M Johnson
(74) Attorney, Agent, or Firm — Morgan, Lewis & Bockius LLP

(57) ABSTRACT

The present disclosure relates to a preparation method of a super absorbent polymer composition. More specifically, it relates to a preparation method of a super absorbent polymer composition capable of pulverizing the hydrogel polymer to a normal particle size without agglomeration between particles by adding an additive having a specific structure, reducing manufacturing cost by simultaneously performing a drying process and a surface cross-linking process, and significantly reducing the amount of fine powder generated during the process.

20 Claims, 2 Drawing Sheets

(56) References Cited

FOREIGN PATENT DOCUMENTS

| | | | |
|---|---|---|---|
| CN | 106661235 A | 5/2017 |
| CN | 107922630 A | 4/2018 |
| CN | 108350189 A | 7/2018 |
| CN | 110312755 A | 10/2019 |
| CN | 111690156 A | 9/2020 |
| EP | 0897304 A1 | 2/1999 |
| EP | 0948997 A2 | 10/1999 |
| EP | 3248991 A1 | 11/2017 |
| EP | 4137539 A1 | 2/2023 |
| GB | 2312213 A | 10/1997 |
| JP | 2009-173920 A | 8/2009 |
| JP | 2011-506493 A | 3/2011 |
| JP | 2011-178969 A | 9/2011 |
| JP | 2012-007062 A | 1/2012 |
| JP | 2013-520464 A | 6/2013 |
| JP | 2013-203842 A | 10/2013 |
| JP | 5756128 B2 | 7/2015 |
| JP | 2017-502108 A | 1/2017 |
| JP | 2018-203997 A | 12/2018 |
| JP | 2022-533035 A | 7/2022 |
| JP | 2022-533561 A | 7/2022 |
| KR | 10-2011-0006771 A | 1/2011 |
| KR | 10-2011-0136597 A | 12/2011 |
| KR | 10-2015-0067729 A | 6/2015 |
| KR | 10-2016-0063975 A | 6/2016 |
| KR | 10-2016-0112220 A | 9/2016 |
| KR | 10-2018-0112110 A | 10/2018 |
| KR | 10-2019-0035314 A | 4/2019 |
| KR | 10-2019-0075574 A | 7/2019 |
| KR | 10-2019-0077359 A | 7/2019 |
| KR | 10-2019-0077541 A | 7/2019 |
| KR | 10-2019-0114777 A | 10/2019 |
| WO | 97/38740 A1 | 10/1997 |
| WO | 2009/076764 A1 | 6/2009 |
| WO | 2011/038374 A2 | 3/2011 |
| WO | 2012/081702 A1 | 6/2012 |
| WO | 2016/148397 A1 | 9/2016 |
| WO | 2016/204302 A1 | 12/2016 |
| WO | 2018/092863 A1 | 5/2018 |
| WO | 2018/120056 A1 | 7/2018 |
| WO | 2019/208905 A1 | 10/2019 |
| WO | 2019/221236 A1 | 11/2019 |

OTHER PUBLICATIONS

International Search Report and Written Opinion issued Apr. 13, 2021 for counterpart International Patent Application No. PCT/KR2020/018644 (See English translations).

International Search Report (with partial translation) and Written Opinion issued in corresponding International Patent Application No. PCT/KR2020/018642, dated Apr. 6, 2021.

Search Report issued in corresponding International Patent Application No. PCT/KR2020/015696, dated Feb. 26, 2021 (partial translation).

Schwalm, "UV Coatings Basics, Recent Developments and New Applications," Elsevier Science, 2007, p. 115.

Odian, "Principles of Polymerization," 2nd Edition, 1981, Wiley, p. 203.

"Fiber-Forming Polymers Recent Advances," Textile Industry Press, p. 416, Jan. 31, 1986. (see English abstract).

[FIG. 1]
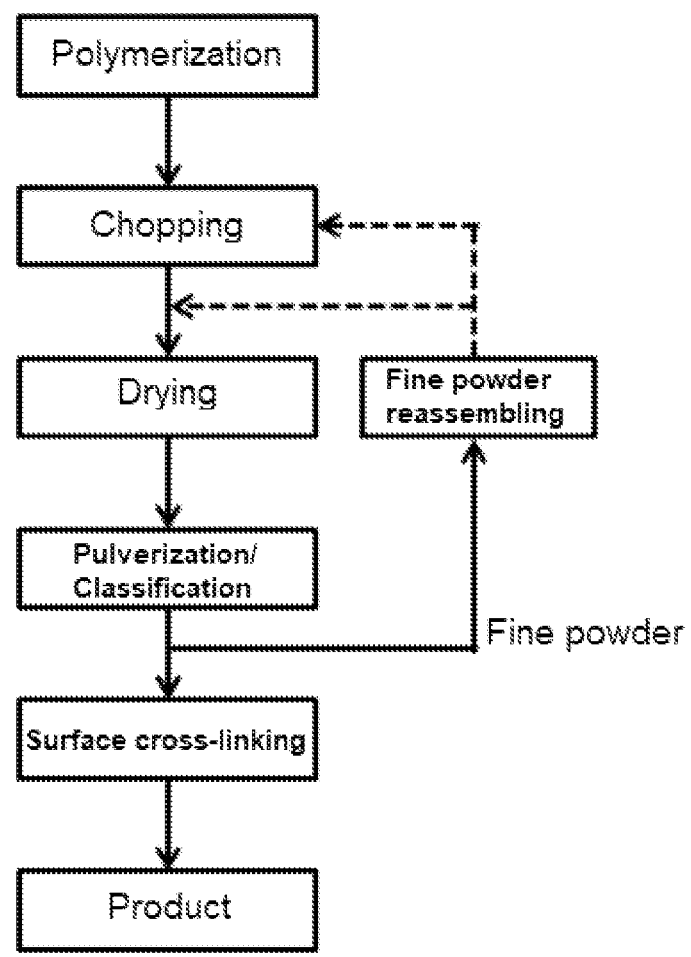

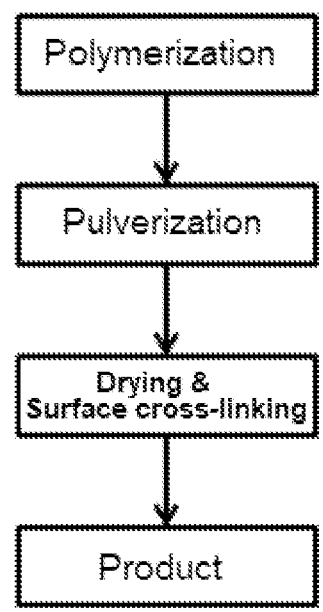
[FIG. 2]

PREPARATION METHOD OF SUPER ABSORBENT POLYMER COMPOSITION

CROSS-REFERENCE TO RELATED APPLICATION(S)

This application claims the benefit of Korean Patent Applications No. 10-2019-0172494 filed on Dec. 20, 2019, No. 10-2020-0148077 filed on Nov. 6, 2020, No. 10-2020-0007115 filed on Jan. 20, 2020 and No. 10-2020-0175606 filed on Dec. 15, 2020 with the Korean Intellectual Property Office, the disclosures of which are incorporated herein by reference in their entirety.

TECHNICAL FIELD

The present disclosure relates to a preparation method of a super absorbent polymer composition. More specifically, it relates to a preparation method of a super absorbent polymer composition in which manufacturing cost is significantly reduced by simultaneously performing a drying process and a surface cross-linking process.

BACKGROUND OF ART

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products, but also for water retaining soil products for gardening, water stop materials for the civil engineering and construction, sheets for raising seedling, fresh-keeping agents for food distribution fields, materials for poultices, or the like.

These super absorbent polymers have been widely used in the field of hygienic materials such as diapers or sanitary napkins. In such hygienic materials, the super absorbent polymer is generally contained in a state of being spread in the pulp. In recent years, however, continuous efforts have been made to provide hygienic materials such as diapers having a thinner thickness. As a part of such efforts, the development of so-called pulpless diapers and the like in which the pulp content is reduced or pulp is not used at all is being actively advanced.

As described above, in the case of hygienic materials in which the pulp content is reduced or the pulp is not used, a super absorbent polymer is contained at a relatively high ratio and these super absorbent polymer particles are inevitably contained in multiple layers in the hygienic materials. In order for the whole super absorbent polymer particles contained in the multiple layers to more efficiently absorb a large amount of liquid such as urine, it is necessary for the super absorbent polymer to basically exhibit high absorption performance as well as fast absorption rate.

Meanwhile, such a super absorbent polymer is generally prepared by the method including a step of polymerizing a monomer to prepare a hydrogel polymer containing a large amount of moisture, and a step of drying the hydrogel polymer, and then pulverizing the dried hydrogel polymer into polymer particles having a desired particle diameter. However, when the hydrogel polymer is dried and then pulverized as described above, a large amount of fine powder is generated, and thus there has been a problem of deteriorating physical properties of the finally produced super absorbent polymer.

In addition, in order to reuse such fine powder, it is common to use a fine powder reassembly which is obtained by mixing the fine powder with water to agglomerate, followed by drying/pulverization/classification. However, due to the water used at this time, a problem such as an increase in energy consumption during the drying process and an increase in a load on the device may occur, and thus productivity in the preparation of the super absorbent polymer may decrease.

Accordingly, there is a continuous demand for the development of a technology capable of manufacturing a super absorbent polymer without generating fine powder, so as to fundamentally solve this problem.

DETAILED DESCRIPTION OF THE INVENTION

Technical Problem

Accordingly, the present disclosure relates to a preparation method of a super absorbent polymer composition capable of pulverizing the hydrogel polymer to a normal particle size without agglomeration between particles by adding an additive having a specific structure, reducing manufacturing cost by simultaneously performing a drying process and a surface cross-linking process, and significantly reducing the amount of fine powder generated during the process.

Technical Solution

In order to solve the above problems, there is provided a preparation method of a super absorbent polymer composition including 1) a step of forming a hydrogel polymer by cross-linking polymerization of a water-soluble ethylene-based unsaturated monomer having at least partially neutralized acidic groups in the presence of an internal cross-linking agent and a polymerization initiator;

2) a step of mixing the hydrogel polymer with a carboxylic acid-based additive, followed by pulverization to prepare a pulverized product containing hydrous super absorbent polymer particles and the additive; and 3) a step of preparing a super absorbent polymer composition containing super absorbent polymer particles having a surface cross-linked layer formed on at least a part of a surface and the additive by mixing a surface cross-linking agent with the pulverized product, followed by drying;

wherein the carboxylic acid-based additive is at least one selected from the group consisting of a carboxylic acid represented by the following Chemical Formula 1 and a salt thereof:

[Chemical Formula 1]

$$A\text{---}(B_1\text{---}B_2)_n\text{---}C$$

in Chemical Formula 1,
A is alkyl having 5 to 21 carbon atoms,
$B_1$ is —OCO—, —COO—, or —COOCH($R_1$)COO—,
$B_2$ is —$CH_2$—, —$CH_2CH_2$—, —CH($R_2$)—, —CH=CH—, or wherein, $R_1$ and $R_2$ are each independently alkyl having 1 to 4 carbon atoms, n is an integer of 1 to 3, and C is a carboxyl group.

Advantageous Effects

The preparation method of a super absorbent polymer composition of the present disclosure can prepare a super absorbent polymer composition consisting of super absorbent polymer particles having a desired particle diameter without agglomeration between pulverized particles by pulverizing a hydrogel polymer in the presence of the carboxylic acid-based additive. In addition, as the hydrogel polymer is pulverized to a normal particle size, the amount of fine powder generated during the manufacture of the super absorbent polymer composition can be significantly reduced, and the manufacturing process is simplified and the manufacturing cost is reduced by performing a drying process and a surface cross-linking process at the same time.

BRIEF DESCRIPTION OF THE DRAWINGS

FIG. 1 is a flow chart illustrating a conventional preparation method of a super absorbent polymer.

FIG. 2 is a flow chart illustrating a preparation method of a super absorbent polymer composition according to an embodiment.

DETAILED DESCRIPTION OF THE EMBODIMENTS

The terminology used herein is for the purpose of describing particular embodiments only and is not intended to be limiting of the invention. The singular forms are intended to include the plural forms as well, unless the context clearly indicates otherwise. It will be further understood that the terms "include", "have", or "possess" when used in this specification, specify the presence of stated features, steps, components, or combinations thereof, but do not preclude the presence or addition of one or more other features, steps, components, or combinations thereof.

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

Hereinafter, the preparation method of a super absorbent polymer and the super absorbent polymer will be described in more detail according to specific embodiments of the present invention.

The terminologies are used merely to refer to specific embodiments, and are not intended to restrict the present disclosure unless it is explicitly expressed. Singular expressions of the present disclosure may include plural expressions unless they are differently expressed contextually.

According to one embodiment of the present disclosure, there is provided a preparation method of a super absorbent polymer composition including 1) a step of forming a hydrogel polymer by cross-linking polymerization of a water-soluble ethylene-based unsaturated monomer having at least partially neutralized acidic groups in the presence of an internal cross-linking agent and a polymerization initiator (step 1);

2) a step of mixing the hydrogel polymer with a carboxylic acid-based additive below, followed by pulverization to prepare a pulverized product containing hydrous super absorbent polymer particles and the additive (step 2); and 3) a step of preparing a super absorbent polymer composition containing super absorbent polymer particles having a surface cross-linked layer formed on at least a part of a surface and the additive by mixing a surface cross-linking agent with the pulverized product, followed by drying (step 3);

wherein the carboxylic acid-based additive is at least one selected from the group consisting of a carboxylic acid represented by the following Chemical Formula 1 and a salt thereof:

[Chemical Formula 1]

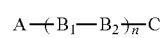

in Chemical Formula 1,

A is alkyl having 5 to 21 carbon atoms, $B_1$ is —OCO—, —COO—, or —COOCH($R_1$)COO—, $B_2$ is —$CH_2$—, —$CH_2CH_2$—, —CH($R_2$)—, —CH=CH—, or wherein, $R_1$ and $R_2$ are each independently alkyl having 1 to 4 carbon atoms, n is an integer of 1 to 3, and C is a carboxyl group.

The terminology "polymer" in the present disclosure is in a state in which a water-soluble ethylene-based unsaturated monomer is polymerized, and may include all moisture content ranges, or all particle diameter ranges. Among the polymers, a polymer having a moisture content of about 30 wt % or more after polymerization and before drying may be referred to as a hydrogel polymer, and particles in which the hydrogel polymer is pulverized and dried may be referred to as a cross-linked polymer.

In addition, the terminology "super absorbent polymer particle" refers to a particulate material containing a cross-linked polymer in which a water-soluble ethylene-based unsaturated monomer having at least partially neutralized acidic groups is polymerized and cross-linked by an internal cross-linking agent.

In addition, the terminology "super absorbent polymer" is used to encompass all of a cross-linked polymer in which a water-soluble ethylene-based unsaturated monomer having at least partially neutralized acidic groups is polymerized or a base resin in the form of powder consisting of super absorbent polymer particles in which the cross-linked polymer is pulverized, and the cross-linked polymer or the base resin further processed, for example, drying, pulverization, classification, surface cross-linking, etc., to be in a state suitable for commercialization, depending on the context. Accordingly, the terminology "super absorbent polymer composition" may be interpreted as encompassing a composition including a super absorbent polymer, that is, a plurality of super absorbent polymer particles.

In addition, the terminology "normal super absorbent polymer particles" refers to particles having a particle diameter of 150 μm to 850 μm among super absorbent polymer particles.

In addition, the terminology "fine powder" refers to particles having a particle diameter of less than 150 μm among super absorbent polymer particles. The particle diameter of these polymer particles can be measured in accordance with EDANA WSP 220.3 by the European Disposables and Nonwovens Association (EDANA).

In addition, the terminology "chopping" refers to cutting the hydrogel polymer into small pieces to increase drying efficiency, and is used separately from pulverization to a normal particle size.

Super absorbent polymers are conventionally prepared by drying a hydrogel polymer and then pulverizing it to a desired particle size. At this time, in order to facilitate drying of the hydrogel polymer and increase an efficiency of the pulverization process, a process of chopping the hydrogel polymer is performed before the drying process. However, due to tackiness of the hydrogel polymer in this chopping process, the hydrogel polymer cannot be pulverized to micro-sized particles and becomes an agglomerated gel. When the agglomerated gel-shaped hydrogel polymer is dried in a fixed-bed type manner, a plate-shaped dried body is formed, and in order to pulverize it to the micro-sized particles, a multi-stage pulverization process is required. Therefore, there has been a problem that many fine powders are generated in this process.

In addition, conventionally, since a surface cross-linking process is separately performed after chopping, drying, and pulverization, energy costs are high in the process, resulting in an increase in manufacturing cost.

Specifically, FIG. 1 shows a flow chart of a conventional preparation method of a super absorbent polymer. Referring to FIG. 1, in the related art, a super absorbent polymer has been prepared including the following steps.

(Polymerization) Cross-linking polymerization of a water-soluble ethylene-based unsaturated monomer having at least partially neutralized acidic groups in the presence of an internal cross-linking agent and a polymerization initiator to form a hydrogel polymer;
(Chopping) Chopping the hydrogel polymer;
(Drying) Drying the chopped hydrogel polymer;
(Pulverization/Classification) Pulverizing the dried polymer, and then classifying the pulverized polymer into normal particles and fine powder; and
(Surface cross-linking) Surface cross-linking the classified normal particles in the presence of a surface cross-linking agent As described above, since the chopped hydrogel polymer has an agglomerated gel shape having a size of about 1 cm to 10 cm, the chopped hydrogel polymer has a plate shape rather than a particle shape after drying. Accordingly, the step of pulverizing the dried polymer, followed by classification has been performed as a step of coarse pulverization, followed by classification and then fine pulverization, followed by classification again so that the produced particles become normal particles, that is, particles having a particle diameter of 150 μm to 850 μm. Since the amount of fine powder separated in the final classification step by this preparation method was as large as about 10 wt % to about 20 wt % based on the total weight of the finally prepared super absorbent polymer, the separated fine powder was mixed with an appropriate amount of water for reassembling, and added to the chopping step or before the drying step.

However, when re-injecting the fine powder reassembly mixed with water into the pulverization or drying process for the reuse of the fine powder, problems such as causing an increase in a load on the device and/or energy consumption have occurred. In addition, physical properties of the super absorbent polymer were deteriorated due to the fine powder that was not classified and remained.

Accordingly, the present inventors have recognized that the amount of fine powder generated in the conventional preparation method is largely influenced by the particle size introduced into the pulverization process, and determined that if the hydrogel polymer can be pulverized to a micro size without agglomeration between the hydrogel polymers in the chopping process, the amount of fine powder generated during the process can be reduced. Accordingly, as a result of experimenting with various types of additives that can lower tackiness of the hydrogel polymer in the chopping process, it was confirmed that when the hydrogel polymer is mixed with the carboxylic acid-based additive and then pulverized, the tackiness of the hydrogel polymer is lowered due to the carboxylic acid-based additive, and thus pulverization is possible into micro-level particles. And from this, the present invention was completed. This is because the carboxylic acid-based additive mixed with the hydrogel polymer is adsorbed on the surface of the hydrogel polymer, thereby preventing agglomeration of the pulverized hydrogel polymers. In addition, since the drying process is performed in the form of micro-sized particles, drying is facilitated and a separate pulverization process is not required after the drying process, so that the amount of fine powder generated can be significantly reduced.

Specifically, FIG. 2 shows a flow chart of a preparation method of a super absorbent polymer composition according to an embodiment. Referring to FIG. 2, unlike in the related art, a hydrogel polymer is prepared and pulverized to a normal particle size, and then subjected to a drying and surface cross-linking process to prepare a super absorbent polymer composition.

Herein, the carboxylic acid-based additive has a hydrophobic functional group and a hydrophilic functional group at the same time. Meanwhile, since the water-soluble ethylene-based unsaturated monomer contains an acidic group (—COOH) and/or a neutralized acidic group (—COO), a large amount of hydrophilic moiety is present on a surface of the hydrogel polymer prepared by polymerization due to the acidic group (—COOH) and/or the neutralized acidic group (—COO⁻) remaining without participating in polymerization. Therefore, when the additive is mixed with the hydrogel polymer, a hydrophilic functional group of the additive is adsorbed to at least some part of the hydrophilic moiety present on the surface of the hydrogel polymer, and the surface of the polymer to which the additive is adsorbed becomes hydrophobic by a hydrophobic functional group located at the other end of the additive. Accordingly, agglomeration between polymer particles can be suppressed.

More specifically, in the carboxylic acid-based additive, the hydrophobic functional group is a alkyl having 5 to 21 carbon atoms group (part A), and the hydrophilic functional group is part C, specifically, a carboxyl group (COOH) or a carboxylate group (—COO⁻) in the case of a salt. The hydrophobic functional group and the hydrophilic functional group are respectively located at both ends of the additive. In particular, the carboxylic acid-based additive further includes part ($B_1$-$B_2$) in addition to part A and part C at both ends, and the part ($B_1$-$B_2$) improves adsorption performance with respect to the polymer surface, which may be insufficient only with the part C. Accordingly, the additive having the structure of Chemical Formula 1 has excellent adsorption performance with respect to the polymer surface exhibiting hydrophilicity compared to the compound having an A-C structure without the part ($B_1$-$B_2$), and thus effectively inhibits agglomeration of the super absorbent polymer particles.

Accordingly, the hydrogel polymer may be pulverized to a normal particle size without agglomeration between particles, and the drying process proceeds after the hydrogel polymer is pulverized to a normal particle size, thereby significantly reducing the amount of fine powder generated during the process. In addition, the preparation method of a super absorbent polymer composition according to an embodiment does not necessarily require a pulverization process and a classification process after drying, and a drying process and a surface cross-linking process are performed together, so that manufacturing cost can be greatly reduced. Further, as a transfer process between the drying process and the surface cross-linking process is eliminated, physical damages on the surface of the particles can be reduced, thereby improving physical properties of the super absorbent polymer prepared in the process.

Specifically, when the hydrogel polymer is pulverized in the presence of the carboxylic acid-based additive, the hydrophobic functional group, part A, contained in the additive imparts hydrophobicity to the surface of the pulverized super absorbent polymer particles, thereby reducing frictional force between the particles and increasing bulk density of the super absorbent polymer. Further, the hydrophilic functional group, part C, contained in the additive is also bonded to the super absorbent polymer particles, so that surface tension of the polymer is not lowered. Accordingly, the super absorbent polymer composition prepared by the above method may exhibit improved surface tension and bulk density compared to a composition not including such an additive.

Hereinafter, the preparation method of a super absorbent polymer composition of one embodiment will be described in more detail for each component.

Step 1

The above step is to form a hydrogel polymer by cross-linking polymerization of a water-soluble ethylene-based unsaturated monomer having at least partially neutralized acidic groups in the presence of an internal cross-linking agent and a polymerization initiator, and may consist of a step of preparing a monomer composition by mixing a water-soluble ethylene-based unsaturated monomer, an internal cross-linking agent and a polymerization initiator, and a step of forming a hydrogel polymer by thermal polymerization or photopolymerization of the monomer composition.

The water-soluble ethylene-based unsaturated monomer may be any monomer commonly used in the preparation of a super absorbent polymer. As a non-limiting example, the water-soluble ethylene-based unsaturated monomer may be a compound represented by the following Chemical Formula 2:

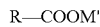 [Chemical Formula 2]

in Chemical Formula 2,

R is a C2 to C5 alkyl group having an unsaturated bond, and

M' is a hydrogen atom, a monovalent or divalent metal, an ammonium group, or an organic amine salt.

Preferably, the monomer may be at least one selected from the group consisting of (meth)acrylic acid, and a monovalent (alkali)metal salt, a divalent metal salt, an ammonium salt and an organic amine salt of the acid.

When (meth)acrylic acid and/or a salt thereof is used as a water-soluble ethylene-based unsaturated monomer, it is advantageous to obtain a super absorbent polymer having improved absorption performance. In addition, maleic anhydride, fumaric acid, crotonic acid, itaconic acid, 2-acryloylethane sulfonic acid, 2-methacryloylethanesulfonic acid, 2-(meth)acryloylpropanesulfonic acid, 2-(meth)acrylamide-2-methyl propane sulfonic acid, (meth)acrylamide, N-substituted (meth)acrylate, 2-hydroxyethyl (meth)acrylate, 2-hydroxypropyl (meth)acrylate, methoxypolyethylene glycol (meth)acrylate, polyethylene glycol (meth)acrylate, (N,N)-dimethylaminoethyl (meth)acrylate, (N,N)-dimethylaminopropyl (meth)acrylamide, or the like may be used as the monomer.

Herein, the water-soluble ethylene-based unsaturated monomer may have acidic groups, and at least some of the acidic groups may be neutralized by a neutralizing agent. Specifically, in the step of mixing the water-soluble ethylene-based unsaturated monomer having acidic groups, the internal cross-linking agent, the polymerization initiator and the neutralizing agent, at least some of the acidic groups of the water-soluble ethylene-based unsaturated monomer may be neutralized. In this case, a basic substance such as sodium hydroxide, potassium hydroxide, and ammonium hydroxide capable of neutralizing acidic groups may be used as the neutralizing agent.

In addition, a degree of neutralization of the water-soluble ethylene-based unsaturated monomer may be 50 to 90 mol %, 60 to 85 mol %, 65 to 85 mol %, or 65 to 75 mol %, wherein the degree of neutralization refers to the degree to which the acidic groups contained in the water-soluble ethylene-based unsaturated monomer are neutralized by the neutralizing agent. A range of the degree of neutralization may vary depending on the final physical properties. An excessively high degree of neutralization causes the neutralized monomers to be precipitated, and thus polymerization may not readily occur. On the contrary, an excessively low degree of neutralization not only deteriorates absorbency of the polymer, but also gives the polymer hard-to-handle properties, such as those of an elastic rubber.

In addition, the terminology 'internal cross-linking agent' used herein is different from a surface cross-linking agent for cross-linking the surface of the super absorbent polymer particles to be described later, and the internal cross-linking agent polymerizes unsaturated bonds of the water-soluble ethylene-based unsaturated monomers by cross-linking. The cross-linking in the above step proceeds regardless of the surface or the inside, but when the surface cross-linking process of the super absorbent polymer particles to be described later is in progress, the surface of the particles of the finally prepared super absorbent polymer has a structure cross-linked by a surface cross-linking agent, and the inside of the particles has a structure cross-linked by the internal cross-linking agent.

As the internal cross-linking agent, any compound may be used as long as it allows the introduction of cross-linking bonds during polymerization of the water-soluble ethylene-based unsaturated monomer. As a non-limiting example, the internal cross-linking agent may be a multifunctional cross-linking agent such as N,N'-methylenebisacrylamide, trimethylolpropane tri(meth)acrylate, ethylene glycol di(meth)acrylate, polyethylene glycol (meth)acrylate, polyethylene glycol di(meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triarylamine, ethylene glycol diglycidyl ether, propylene glycol, glycerin, or ethylene carbonate, and theses may be used alone or in combination of two or more. However, the present disclosure is not limited thereto. Preferably, polyethylene glycol diacrylate may be used.

The cross-linking polymerization of the water-soluble ethylene-based unsaturated monomer in the presence of the internal cross-linking agent may be performed by thermal polymerization, photopolymerization or hybrid polymerization in the presence of a polymerization initiator with or without a thickener, a plasticizer, a preservation stabilizer, an antioxidant, etc., but the specific details will be described later.

In the monomer composition, the internal cross-linking agent may be used in an amount of 0.01 to 5 parts by weight based on 100 parts by weight of the water-soluble ethylene-based unsaturated monomer. For example, the internal cross-linking agent may be used in an amount of 0.01 parts by weight or more, 0.05 parts by weight or more, 0.1 parts by weight or more or 0.2 parts by weight or more, and 5 parts by weight or less, 3 parts by weight or less, 2 parts by weight or less, 1 parts by weight or less, or 0.5 parts by weight or less based on 100 parts by weight of the water-soluble ethylene-based unsaturated monomer. When too little internal cross-linking agent is used, cross-linking does not occur sufficiently, and thus it may be difficult to achieve strength above an appropriate level, and when too much internal cross-linking agent is used, the internal cross-linking density increases, and thus it may be difficult to achieve a desired level of water retention capacity.

In addition, the polymerization initiator may be properly selected depending on the polymerization method. In the case of a thermal polymerization, a thermal polymerization initiator is used, and in the case of a photopolymerization, a photopolymerization initiator is used. Further, in the case of a hybrid polymerization method (a method using both heat and light), all of the thermal polymerization initiator and the photopolymerization initiator can be used. However, even by the photopolymerization method, a certain amount heat is generated by UV radiation and the like, and some heat occurs as the polymerization reaction, an exothermal reaction, progresses. Therefore, the composition may additionally include the thermal polymerization initiator.

Herein, any compound which can form a radical by light such as UV rays may be used as the photopolymerization initiator without limitation.

For example, the photopolymerization initiator may be one or more compounds selected from the group consisting of benzoin ether, dialkyl acetophenone, hydroxyl alkylketone, phenyl glyoxylate, benzyl dimethyl ketal, acyl phosphine, and α-aminoketone. Further, specific examples of the acyl phosphine include diphenyl(2,4,6-trimethylbenzoyl) phosphine oxide, phenylbis(2,4,6-trimethylbenzoyl)phosphine oxide, ethyl(2,4,6-trimethylbenzoyl)phenylphosphinate, and the like. More various photopolymerization initiators are well disclosed in "UV Coatings: Basics, Recent Developments and New Application (Elsevier, 2007)" written by Reinhold Schwalm, p 115, and the present disclosure is not limited thereto.

Furthermore, as the thermal polymerization initiator, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate (($NH_4)_2S_2O_8$), and the like may be used as examples of the persulfate-based initiators; and 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane] dihydrochloride, 4,4-azobis-(4-cyanovaleric acid), and the like may be used as examples of the azo-based initiators. More various thermal polymerization initiators are well disclosed in 'Principle of Polymerization (Wiley, 1981)' written by Odian, p 203, and the present disclosure is not limited thereto.

The polymerization initiator may be used in an amount of 2 parts by weight or less based on 100 parts by weight of the water-soluble ethylene-based unsaturated monomer. When the concentration of the polymerization initiator is excessively low, the polymerization rate becomes slow, and a large amount of residual monomers may be extracted from the final product. Conversely, when the concentration of the polymerization initiator is higher than the above range, polymer chains forming a network are shortened, so that the content of extractable components increases and absorbency under pressure decreases, thereby lowering physical properties of the polymer.

The monomer composition may further include an additive such as a thickener, a plasticizer, a preservation stabilizer, an antioxidant, and the like, if necessary.

In addition, the monomer composition containing the monomer may be, for example, in the form of a solution dissolved in a solvent such as water. The solid content of the monomer composition in a solution state, that is, the concentration of the monomer, the internal cross-linking agent, and the polymerization initiator may be appropriately adjusted in consideration of the polymerization time and reaction conditions. For example, the solid content of the monomer composition may be 10 to 80 wt %, 15 to 60 wt %, or 30 to 50 wt %.

When the monomer composition has the solid content in the above range, it may be advantageous for controlling the pulverization efficiency during pulverization of the polymer to be described later while eliminating the need to remove unreacted monomers after polymerization by using a gel effect phenomenon occurring in the polymerization reaction of a high-concentration aqueous solution.

At this time, any solvent which can dissolve the above components may be used without limitation. For example, the solvent may be in combination of at least one selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, and N,N-dimethylacetamide.

Meanwhile, the cross-linking polymerization of a water-soluble ethylene-based unsaturated monomer having at least partially neutralized acidic groups may be performed without any particular limitation, as long as the hydrogel polymer can be formed by thermal polymerization, photopolymerization, or hybrid polymerization.

Specifically, the polymerization method is largely divided into thermal polymerization and photopolymerization depending on an energy source of the polymerization. In the case of thermal polymerization, it is generally carried out in a reactor equipped with an agitation spindle, such as a kneader. In the case of photopolymerization, it is generally carried out in a reactor equipped with a movable conveyor belt, or in a container with a flat bottom. However, the above-mentioned polymerization method is merely an example, and the present disclosure is not limited thereto.

For example, a hydrogel polymer may be obtained by supplying hot air to the reactor with an agitation spindle such as a kneader or heating the reactor to perform thermal polymerization. The hydrogel polymer thus obtained may have a size of several centimeters to several millimeters, according to the shape of the agitation spindle equipped in the reactor. Specifically, the size of the obtained hydrogel polymer may vary depending on the concentration and injection speed of the monomer composition injected thereto, and a hydrogel polymer having a weight average particle diameter of 2 to 50 mm may be obtained.

Further, when the photopolymerization is carried out in a reactor equipped with a movable conveyor belt or in a container with a flat bottom as described above, the obtained hydrogel polymer may be usually a sheet-like hydrogel polymer having a width of the belt. In this case, the thickness of the polymer sheet may vary depending on the concentration, injection speed or injection amount of the monomer composition to be injected, but usually, it is preferable to feed the monomer composition such that a sheet-like polymer having a thickness of about 0.5 to about 5 cm can be obtained. When the monomer composition is fed such that the thickness of the sheet-like polymer becomes too thin, the production efficiency is low, which is undesirable. When the thickness of the sheet-like polymer is greater than 5 cm, the polymerization reaction cannot be evenly carried out over the entire thickness because of the excessive thickness.

At this time, the hydrogel polymer thus obtained may have a moisture content of 30 to 70 wt %. For example, the moisture content of the hydrogel polymer may be 30 wt % or more, 40 wt % or more, or 50 wt % or more, and 70 wt % or less, 65 wt % or less, or 60 wt % or less. When the moisture content of the hydrogel polymer is too low, it is difficult to secure an appropriate surface area in the subsequent pulverization step, and thus the pulverization may not be effective. When the moisture content of the hydrogel polymer is too high, the pressure received in the subsequent pulverization step increases, and thus the pulverization may be difficult to proceed to a desired particle size.

Meanwhile, the "moisture content" in the present description is the content of moisture in the entire weight of the hydrogel polymer, and it means a value of which the weight of the dried polymer is subtracted from the weight of the hydrogel polymer. Specifically, the moisture content is defined as a value calculated by the weight loss due to moisture evaporation from the polymer in the process of increasing the temperature of the crumb polymer for drying through infrared heating. At this time, the drying conditions for measuring the moisture content are as follows: the temperature is increased to about 180° C. and maintained at 180° C., and the total drying time is 40 min including 5 min of a heating step.

The hydrogel polymer formed by the step 1 may have a three-dimensional network structure in which main chains formed by polymerization of the water-soluble ethylene-based unsaturated monomers are cross-linked by the internal cross-linking agent. When the hydrogel polymer has a three-dimensional network structure, water retention capacity and absorbency under pressure, which are general physical properties of the super absorbent polymer, can be significantly improved compared to the case of having a two-dimensional linear structure that is not further cross-linked by the internal cross-linking agent.

Step 2

The above step is to mix the hydrogel polymer with the carboxylic acid-based additive, followed by pulverization to prepare a pulverized product containing hydrous super absorbent polymer particles and the additive. In this step, the hydrous gel polymer is not chopped, but pulverized to a particle size of about 150 μm to about 850 μm, thereby preparing hydrous super absorbent polymer particles that can be applied to the final product, and the carboxylic acid-based additive is used for this.

At this time, the carboxylic acid-based additive is at least one selected from the group consisting of a carboxylic acid represented by the Chemical Formula 1 and a metal salt thereof. Specifically, the carboxylic acid-based additive is at least one selected from the group consisting of a carboxylic acid represented by the Chemical Formula 1, an alkali metal salt of a carboxylic acid represented by the Chemical Formula 1, and an alkaline earth metal salt of a carboxylic acid represented by the Chemical Formula 1. More specifically, the carboxylic acid-based additive is one of a carboxylic acid represented by the Chemical Formula 1, an alkali metal salt of a carboxylic acid represented by the Chemical Formula 1, and an alkaline earth metal salt of a carboxylic acid represented by the Chemical Formula 1.

In the Chemical Formula 1, A is a hydrophobic moiety and may be a linear or branched alkyl group having 5 to 21 carbon atoms. However, the case where A is a linear alkyl group is more advantageous in terms of suppressing agglomeration of pulverized particles and improving dispersibility. When A is an alkyl group having less than 5 carbon atoms, there is a problem in that the chain is short, so that the agglomeration of pulverized particles cannot be effectively controlled. When A is an alkyl group having more than 21 carbon atoms, mobility of the additive may be reduced, so that the carboxylic acid-based additive may not be effectively mixed with the hydrogel polymer and the cost of the composition may increase due to an increase in the cost of the additive.

Specifically, in the Chemical Formula 1, A may be linear alkyl having 5 to 21 carbon atoms such as n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-icosanyl, or n-heneicosanyl.

More specifically, A may be linear alkyl having 6 to 18 carbon atoms. For example, A may be —$C_6H_{13}$, —$C_{11}H_{23}$, —$C_{12}H_{25}$, —$C_{17}H_{35}$, or —$C_{18}H_{37}$.

In addition, part ($B_1$-$B_2$) of the Chemical Formula 1 improves adsorption performance with respect to the polymer surface, which may be insufficient only with the part C. When the number of carbon atoms of $B_2$ is 3 or more, the distance between part $B_1$ and part C increases, and the adsorption performance with respect to the hydrogel polymer may be deteriorated.

Herein, $R_1$ and $R_2$ may each independently be linear or branched alkyl having 1 to 4 carbon atoms. More specifically, $R_1$ and $R_2$ may each independently be methyl, ethyl, propyl, isopropyl, butyl, isobutyl, sec-butyl, or tert-butyl. Since the additive can be adsorbed on the super absorbent polymer particles, it is advantageous that the molecular structure of the additive is not bulky, and thus both $R_1$ and $R_2$ may be methyl.

In addition, n of the Chemical Formula 1 may be 1, 2, or 3. More specifically, n, which means the number of ($B_1$-$B_2$), is preferably 1, considering that the part ($B_1$-$B_2$) is for reinforcing adsorption performance with respect to part C and how long a molecular length is required in order for the carboxylic acid-based additive to be effectively adsorbed on the hydrogel polymer.

Specifically, in the Chemical Formula 1, $B_1$ may be

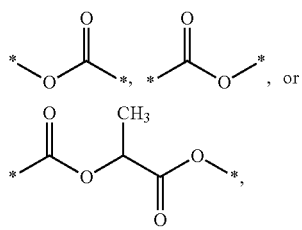

wherein * is a bonding site with a neighboring atom.

For example, $B_1$ may be

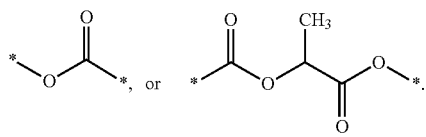

In addition, in the Chemical Formula 1, $B_2$ may be

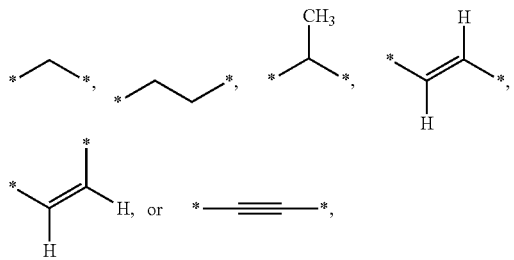

wherein * is a bonding site with a neighboring atom. At this time, in order to improve adsorption performance of the additive with respect to the cross-linked polymer together with part C, $B_2$ is preferably

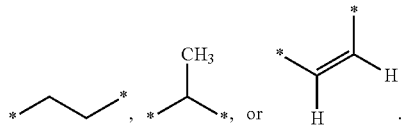

In addition, in the Chemical Formula 1, part C is a carboxyl group (COOH) as a hydrophilic moiety, and when the carboxylic acid-based additive is a salt, the hydrophilic moiety is a carboxylate group (COO⁻).

In other words, the carboxylic acid-based additive may be a compound represented by the following Chemical Formula 1a:

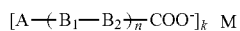
[Chemical Formula 1a]

in Chemical Formula 1a,

M is $H^+$, a monovalent cation of an alkali metal, or a divalent cation of an alkaline earth metal, k is 1 if M is $H^+$ or a monovalent cation of an alkali metal, and 2 if it is a divalent cation of an alkaline earth metal, and descriptions of A, $B_1$, $B_2$ and n are as defined in the Chemical Formula 1.

More specifically, when the carboxylic acid-based additive is an alkali metal salt of the carboxylic acid represented by the Chemical Formula 1, the additive may be represented by the following Chemical Formula 1':

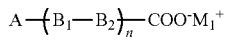
[Chemical Formula 1']

in Chemical Formula 1', $M_1$ is an alkali metal such as sodium or potassium, and descriptions of A, $B_1$, $B_2$ and n are as defined in the Chemical Formula 1.

In addition, when the carboxylic acid-based additive is an alkaline earth metal salt of the carboxylic acid represented by the Chemical Formula 1, the additive may be represented by the following Chemical Formula 1":

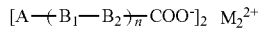
[Chemical Formula 1"]

in Chemical Formula 1", $M_2$ is an alkaline earth metal such as calcium, and descriptions of A, $B_1$, $B_2$ and n are as defined in the Chemical Formula 1.

For example, the carboxylic acid-based additive may be any one carboxylic acid selected from the group consisting of:

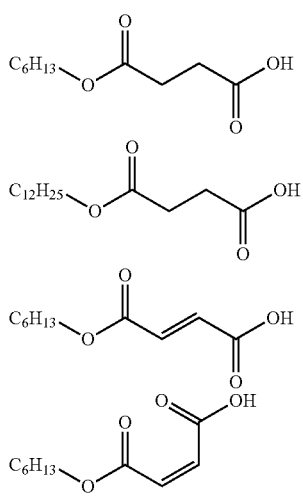

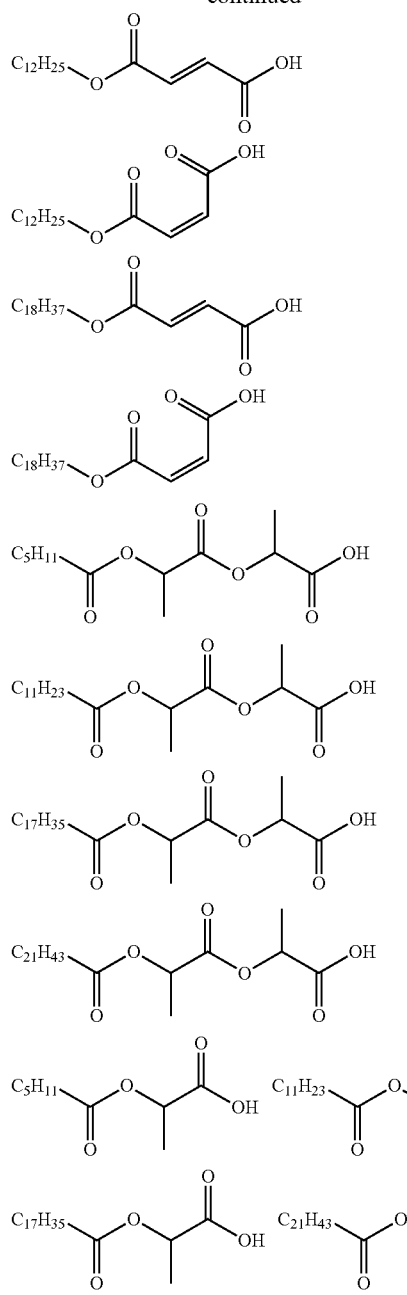
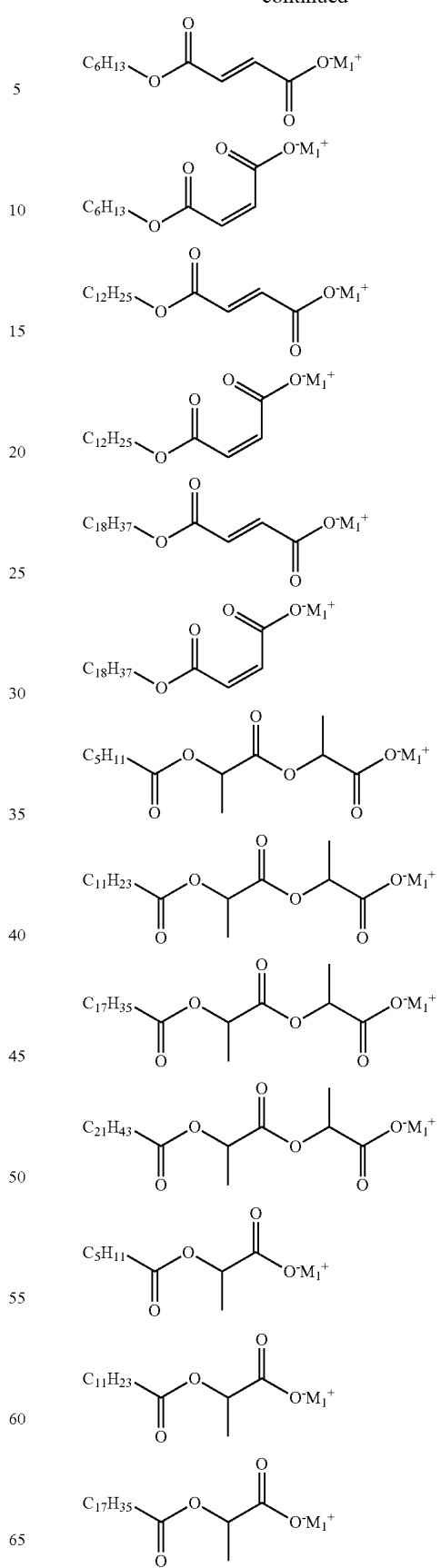
Alternatively, the carboxylic acid-based additive may be any one alkali metal salt selected from the group consisting of:
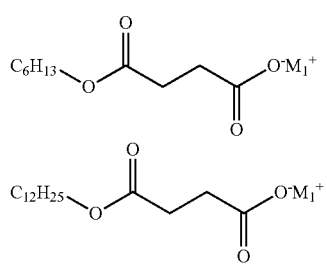

-continued

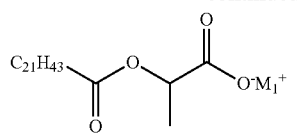

In the above, $M_1$ is each independently an alkali metal.

Alternatively, the carboxylic acid-based additive may be any one alkaline earth metal salt selected from the group consisting of:

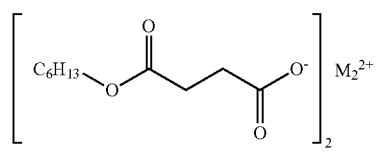

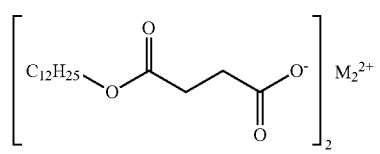

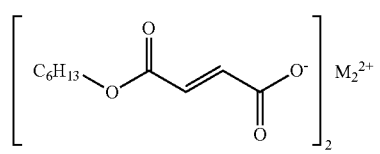

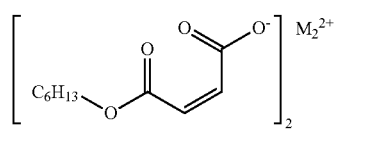

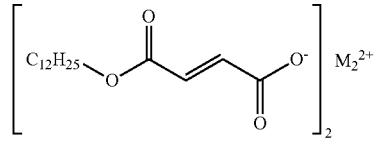

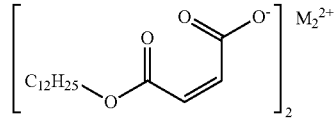

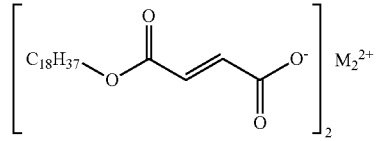

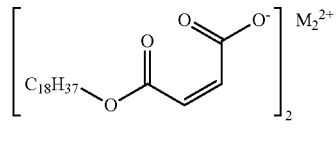

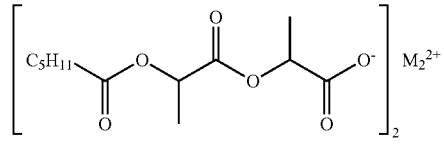

-continued

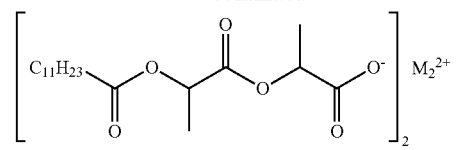

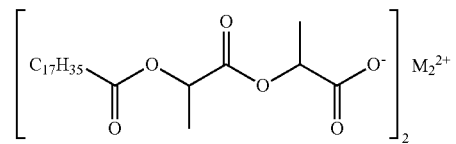

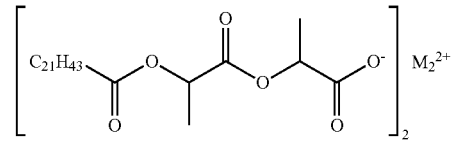

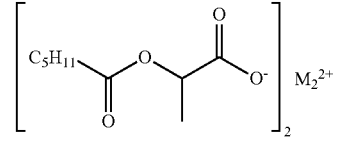

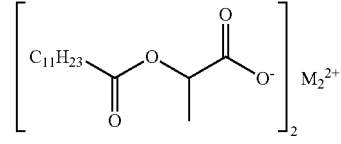

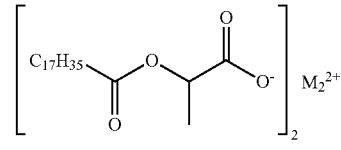

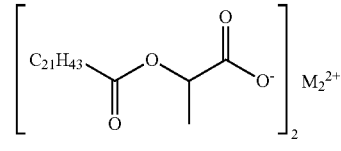

In the above, $M_2$ is each independently an alkaline earth metal.

For example, the carboxylic acid-based additive may be any one of compounds represented by the following Chemical Formulae 1-1 to 1-7, but is not limited thereto:

1-1

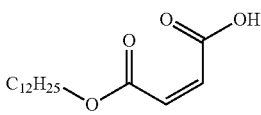

1-2

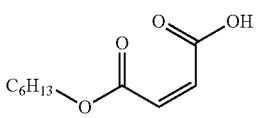

1-3

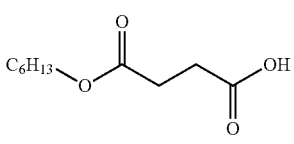

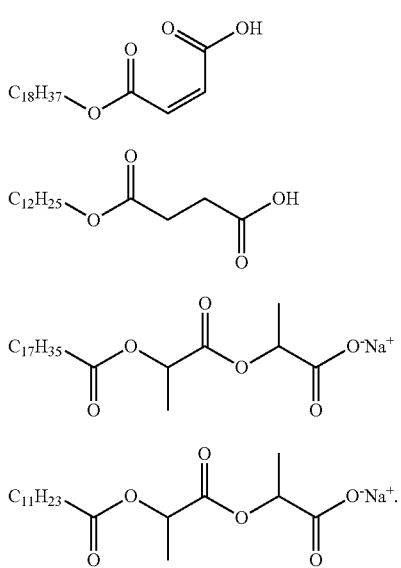

Meanwhile, the carboxylic acid-based additive may be used in an amount of about 0.01 to about 10 parts by weight based on 100 parts by weight of the hydrogel polymer. When too little additive is used, the particles may not be evenly adsorbed on the surface of the hydrogel polymer, resulting in re-agglomeration of the particles after pulverization, and when too much additive is used, the overall physical properties of the final super absorbent polymer may decrease. For example, the carboxylic acid-based additive may be used in an amount of 0.01 parts by weight or more, 0.015 parts by weight or more, or 0.1 parts by weight or more, and 5 parts by weight or less, 3 parts by weight or less, 2 parts by weight or less, or 1 parts by weight or less based on 100 parts by weight of the hydrogel polymer.

The method of mixing the additive with the hydrogel polymer is not particularly limited, and may be appropriately selected as long as it is a method capable of evenly mixing the additive with the hydrogel polymer. Specifically, the additive may be dry-mixed, dissolved in a solvent and then mixed, or melted and then mixed.

For example, the additive may be mixed in the form of a solution dissolved in a solvent. At this time, water may be used as the solvent in consideration of the ease of drying and the cost of solvent recovery system. In addition, a method of putting the additive in the form of a solution and the hydrogel polymer in a reaction tank for mixing, a method of spraying the solution after putting the hydrogel polymer in a mixer, a method of continuously supplying the hydrogel polymer and the solution to a continuously operating mixer for mixing, or the like may be used.

A pulverized product containing hydrous super absorbent polymer particles and the additive may be prepared by mixing the hydrogel polymer with the additive, followed by pulverization. Specifically, the pulverization step may be performed so that the pulverized hydrous super absorbent polymer particles have a normal particle size.

Herein, the pulverizing machine used for pulverization is not particularly limited. Specifically, it may include at least one selected from the group consisting of a vertical pulverizer, a turbo cutter, a turbo grinder, a rotary cutter mill, a cutter mill, a disc mill, a shred crusher, a crusher, a chopper, and a disc cutter, but the present disclosure is not limited thereto.

Alternatively, a pin mill, a hammer mill, a screw mill, a roll mill, a disc mill, or a jog mill may be also used as the pulverizing machine, but the present disclosure is not limited thereto.

Among them, the pulverization may be performed by a chopper, more specifically by a meat chopper. At this time, the meat chopper includes two or more perforated plates. More specifically, the meat chopper includes a chopping module including two or more perforated plates, and each of the two or more perforated plates may have a plurality of fine chopping holes having a certain size through which the hydrogel polymer can pass. In addition, a hole size of each fine chopping hole in the perforated plates may be 0.2 mm to 5 mm. In other words, it can be seen that the pulverization is performed by pushing the hydrogel polymer mixed with the additive so that the hydrogel polymer is pulverized while passing through the fine chopping holes of perforated plates. At this time, an extruder may be used to push out the hydrogel polymer. For example, a single- or multiple-screw extruder may be used.

For example, the hydrogel polymer mixed with the carboxylic acid-based additive may be pulverized using a meat chopper including a first perforated plate and a second perforated plate. The hole sizes (meaning a diameter of the hole) of the fine chopping holes provided in each of the first and second perforated plates may be the same or different from each other. At this time, for ease of pulverization, it is preferable that the hole size of the fine chopping holes provided in the second perforated plate is smaller than the hole size of the fine chopping holes provided in the first perforated plate. For example, the hole size of the fine chopping holes provided in the first perforated plate may be about 1.5 mm to about 5 mm, and the hole size of the fine chopping holes provided in the second perforated plate may be about 0.2 mm to about 1.2 mm.

When pulverization is performed by passing the hydrogel polymer mixed with the carboxylic acid-based additive through a first perforated plate having a plurality of fine chopping holes having a hole size of 1.5 mm to 5 mm, and then passing it through a second perforated plate having a plurality of fine chopping holes having a hole size of 0.2 mm to 1.2 mm, a particle size distribution similar to that of the product after drying is achieved, so that a process of pulverizing the dried body can be omitted, thereby fundamentally preventing the generation of fine powder.

Herein, the "hydrous super absorbent polymer particles" contained in the pulverized product are particles having a moisture content of about 30 wt % or more. Since they are particles in which the hydrogel polymer is pulverized into particles without a drying process, they may have a moisture content of 30 to 70 wt %, like the hydrogel polymer.

In addition, the hydrous super absorbent polymer particles may have a particle size of normal particles, that is, a particle diameter of 150 μm to 850 μm. Specifically, the pulverized product may contain 90 wt % or more, 92 wt % or more, 93 wt % or more, 94 wt % or more, or 95 wt % or more of hydrous super absorbent polymer particles having a particle diameter of 150 μm to 850 μm based on the total weight. This particle diameter may be measured in accordance with EDANA WSP 220.3 by the European Disposables and Nonwovens Association (EDANA). Alternatively, the content of hydrous super absorbent polymer particles having a particle diameter of 150 μm to 850 μm in the pulverized product may be considered to be the same as the content of super absorbent polymer particles having a particle diameter of 150 μm to 850 μm in the finally prepared super absorbent polymer composition, considering that no additional pulverization process is performed after the drying and surface cross-linking process in the preparation of the super absorbent polymer composition.

Meanwhile, at least some of the additive contained in the pulverized product may be present on a surface of the hydrous super absorbent polymer particles. Herein, "at least some of the additive is present on a surface of the hydrous super absorbent polymer particles" means that at least some of the additive is adsorbed or bonded on the surface of the hydrous super absorbent polymer particles. Specifically, the additive may be physically or chemically adsorbed on the surface of the super absorbent polymer. More specifically, the hydrophilic functional group of the additive may be physically adsorbed on the hydrophilic moiety of the surface of the super absorbent polymer by an intermolecular force such as dipole-dipole interaction. In this way, the hydrophilic moiety of the additive is physically adsorbed on the surface of the super absorbent polymer particles to surround the surface, and the hydrophobic moiety of the additive is not adsorbed on the surface of the polymer particles, so the polymer particles may be coated with the additive in the form of a micelle structure. This is because the carboxylic acid-based additive is not added during the polymerization process of the water-soluble ethylene-based unsaturated monomer, but is added after the polymer is formed. Accordingly, the phenomenon of re-agglomeration between the hydrous super absorbent polymer particles may be further suppressed, compared to the case where the additive is added during the polymerization process and present inside the polymer.

Step 3

The above step is to prepare a super absorbent polymer composition containing super absorbent polymer particles having a surface cross-linked layer formed on at least a part of a surface and the additive by mixing a surface cross-linking agent with the pulverized product, followed by drying. This step forms a surface cross-linked layer on the surface of the super absorbent polymer particles while drying the hydrous super absorbent polymer particles contained in the pulverized product in the presence of a surface cross-linking agent.

Specifically, drying of the pulverized product may be performed such that the moisture content of each of the plurality of super absorbent polymer particles contained in the prepared super absorbent polymer composition is about 10 wt % or less, specifically, about 0.01 to about 10 wt %.

In addition, the cross-linked polymer included in the super absorbent polymer particles may be further cross-linked with a surface cross-linking agent, so that a surface cross-linked layer may be formed on at least a part of the surface of the super absorbent polymer particles. This is to increase a surface cross-linking density of super absorbent polymer particles, and when the super absorbent polymer particles further include a surface cross-linked layer as described above, they may have a structure having higher cross-linking density on the outside than inside.

As the surface cross-linking agent, any surface cross-linking agent that has been conventionally used in the preparation of a super absorbent polymer may be used without any particular limitation. Examples of the surface cross-linking agent may include at least one polyol selected from the group consisting of ethylene glycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; at least one carbonate-based compound selected from the group consisting of ethylene carbonate, propylene carbonate, and glycerol carbonate; an epoxy compound such as ethylene glycol diglycidyl ether; an oxazoline compound such as oxazolidinone; a polyamine compound; an oxazoline compound; a mono-, di- or poly-oxazolidinone compound; a cyclic urea compound; and the like.

Specifically, as the surface cross-linking agent, one or more, two or more, or three or more of the aforementioned surface cross-linking agents may be used. For example, propylene glycol and ethylene carbonate may be used together.

This surface cross-linking agent may be used in an amount of about 0.001 to about 5 parts by weight based on 100 parts by weight of the pulverized product. For example, the surface cross-linking agent may be used in an amount of 0.005 parts by weight or more, 0.01 parts by weight or more, or 0.05 parts by weight or more, and 5 parts by weight or less, 3 parts by weight or less, or 1 parts by weight or less based on 100 parts by weight of the pulverized product. By adjusting the content of the surface cross-linking agent within the above-described range, a super absorbent polymer having excellent absorption properties can be prepared.

In addition, it may be performed by adding an inorganic material in addition to the surface cross-linking agent. That is, in the presence of the surface cross-linking agent and the inorganic material, the step of forming a surface cross-linked layer by further cross-linking the surface of the hydrous super absorbent polymer particles may be performed.

As the inorganic material, at least one inorganic material selected from the group consisting of silica, clay, alumina, silica-alumina composite, titania, zinc oxide and aluminum sulfate may be used. The inorganic material may be used in a powdery form or in a liquid form, and in particular, alumina powder, silica-alumina powder, titania powder, or nanosilica solution may be used. In addition, the inorganic material may be used in an amount of about 0.001 to about 1 parts by weight based on 100 parts by weight of the pulverized product.

In addition, the method of mixing the surface cross-linking agent with the pulverized product is not particularly limited. For example, a method of adding the surface cross-linking agent and the pulverized product in a reactor for mixing, a method of spraying the surface cross-linking agent onto the pulverized product, or a method of mixing the pulverized product and the surface cross-linking agent while continuously providing them to a continuously operating mixer may be used.

When mixing the surface cross-linking agent and the pulverized product, water and/or methanol may be further mixed therewith. When water and methanol are added thereto, there is an advantage that the surface cross-linking agent may be evenly dispersed in the super absorbent polymer composition. Alternatively, the surface cross-linking agent may be mixed in the form of a solution dissolved in water and/or methanol. At this time, amounts of water and methanol to be added may be properly controlled for the purposes of inducing a uniform dispersion of the surface cross-linking agent, preventing an agglomeration phenomenon of the super absorbent polymer composition, and optimizing a surface penetration depth of the surface cross-linking agent.

The drying and surface cross-linking process may be performed in a moving type manner. The moving type drying is classified from a fixed-bed type drying according to whether or not materials flow during drying.

Specifically, the moving-type drying refers to a method of drying a material to be dried while mechanically stirring it. At this time, the direction in which hot air passes through the material may be the same as or different from the circulation direction of the material. Alternatively, the material may be circulated inside the dryer, and dried by passing heat transfer fluids through a separate pipe outside the dryer.

On the other hand, the fixed-bed type drying refers to a method in which a material to be dried is fixed on a floor such as a porous iron plate through which air can pass, and hot air passes through the material from bottom to top to dry.

Therefore, it is preferable to dry the pulverized product in a moving-type drying manner from the viewpoint of preventing agglomeration between the hydrous super absorbent polymer particles in the pulverized product to be dried in the above step and completing the drying in a short time.

As a device capable of drying by such a moving-type drying manner, a horizontal-type mixer, a rotary kiln, a paddle dryer, a steam tube dryer, or a generally used moving-type dryer can be used.

The means for increasing the temperature in the dryer is not particularly limited. It is possible to provide a thermal media thereto or provide a heat source directly thereto. At this time, usable thermal media may be a heated fluid such as steam, hot air, hot oil, and the like, but the present invention is not limited thereto. Furthermore, the temperature of the thermal media provided thereto may be properly selected in consideration of the means of the thermal media, heating speed, and target temperature of heating. Meanwhile, an electric heater or a gas heater may be used as the heat source provided directly, but the present invention is not limited thereto.

In addition, in order to perform the drying process and the surface cross-linking process at the same time, the drying may be performed at a temperature of 80° C. to 250° C. for 10 minutes to 3 hours.

Specifically, the temperature in the dryer may be 80° C. to 250° C. When the temperature in the dryer is too low, the drying time may become excessively long, and when the drying temperature is too high, only the surface of the polymer is dried and the physical properties of the final super absorbent polymer may decrease. Therefore, the drying process may be preferably carried out at a temperature in the dryer of about 100° C. to about 240° C., more preferably at a temperature of about 150° C. to about 220° C.

Furthermore, the drying time may be about 10 minutes to about 100 minutes, or about 30 minutes to about 80 minutes in consideration of process efficiency.

Meanwhile, at least some of the additive contained in the super absorbent polymer composition may be present on a surface of the super absorbent polymer particles. Accordingly, the additive may be adsorbed or bonded on at least a part of the surface of the prepared super absorbent polymer particles, and a surface cross-linked layer may be formed on the other part.

In addition, the super absorbent polymer composition prepared by the above method may further include a compound formed by decomposing an ester bond of $B_1$ in the process of drying after the additive is pulverized with the hydrogel polymer, in addition to the super absorbent polymer particles and the carboxylic acid-based additive.

Specifically, when the additive is a compound in which n is 1 and $B_1$ is —OCO—, the super absorbent polymer composition may further include an alcohol having an A-OH structure and a compound having a HOOC—$B_2$—C structure.

In addition, when the additive is a compound in which n is 1 and $B_1$ is —COO—, the super absorbent polymer composition may further include a carboxylic acid having an A-COOH structure and a compound having a HO—$B_2$—C structure.

In addition, when the additive is a compound in which n is 1 and $B_1$ is —COOCH($R_1$)COO—, the super absorbent polymer composition may further include a carboxylic acid having an A-COOH structure and a compound having a HOCH($R_1$)COO—$B_2$—C structure.

As the super absorbent polymer composition further includes the compound formed by decomposing an ester bond in the additive molecule, mobility of the additives is increased, and a phenomenon of re-agglomeration after pulverization can be further prevented.

In addition, a compound having a glucose unit containing a plurality of hydroxyl groups in the molecule such as microcrystalline cellulose may not be used in the above preparation method. For example, when the super absorbent polymer composition includes microcrystalline cellulose having an average particle diameter of 1 to 10 μm such as AVICEL® PH-101 represented by the following Chemical Formula 3 available from FMC, agglomeration between the finally prepared super absorbent polymer particles may not be suppressed due to the plurality of hydroxyl groups, and thus the effect by the above-described additive may not be effectively expressed.

[Chemical Formula 3]

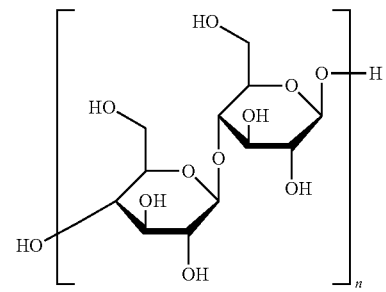

As described above, most of the super absorbent polymer composition prepared according to an embodiment is normal particles and has a low fine powder content, and thus an additional pulverization step may not be included after drying the pulverized product. Accordingly, an additional classification step may not be included. That is, it is possible to prepare a super absorbent polymer composition that can be applied to a product without an additional pulverization/classification step, but a fine pulverization process or a classification process may be additionally performed depending on the purpose and need to which the product is applied.

Meanwhile, the super absorbent polymer composition prepared by the above method has a low fine powder content without a separate classification process, and may have similar or higher water retention capacity (CRC) and absorbency under pressure (AUP), which are general physical properties, compared to the super absorbent polymer composition prepared by the conventional method. In addition, the super absorbent polymer composition is characterized in that it has an equivalent level of surface tension while having high bulk density. This is because the hydrophobic functional group, part A, contained in the carboxylic acid-based additive imparts hydrophobicity to the surface of the pulverized super absorbent polymer particles, thereby reducing frictional force between the particles and increasing bulk density of the super absorbent polymer. Further, the hydrophilic functional group, part C, contained in the additive is also bonded to the super absorbent polymer particles, so that surface tension of the polymer is not lowered.

Specifically, the super absorbent polymer composition prepared as described above may contain 90 wt % or more, 91 wt % or more, or 91.5 wt % or more of super absorbent polymer particles having a particle diameter of 150 μm to 850 μm, that is, normal particles, based on the total weight.

In addition, the super absorbent polymer composition may contain less than about 10 wt %, specifically less than about 5 wt %, more specifically less than about 4 wt %, more specifically less than about 3 wt % of fine powder having a particle diameter of less than 150 μm based on the total weight. This is in contrast to having fine powder of about 10 wt % to about 20 wt % when the hydrogel polymer is dried and then pulverized to prepare a super absorbent polymer.

In addition, the super absorbent polymer composition may have centrifuge retention capacity (CRC) of 25 g/g or more, 27 g/g or more, or 28 g/g or more, and 45 g/g or less, when measured in accordance with the EDANA method WSP 241.3.

In addition, the super absorbent polymer composition may have absorbency under pressure (AUP) at 0.7 psi of 18 g/g or more, 19 g/g or more, or 20 g/g or more, and 26 g/g or less, 25 g/g or less, or 24 g/g or less, when measured in accordance with the EDANA method WSP 242.3.

In addition, the super absorbent polymer composition may have a bulk density of 0.5 to 0.8 g/ml. At this time, for measuring the bulk density, about 100 g of the super absorbent polymer composition was put into a funnel-type bulk density measuring device, flowed down into a 100 ml container, and the weight of the super absorbent polymer contained in the container was measured. That is, the bulk density is calculated as (weight of super absorbent polymer composition)/(container volume, 100 ml). More specifically, the super absorbent polymer composition may have a bulk density of 0.65 to 0.73 g/ml, or 0.68 to 0.72 g/ml.

In addition, the super absorbent polymer composition may have a surface tension of 68 mN/m or more and less than 72 mN/m. At this time, the surface tension may be measured for the brine containing swollen super absorbent resin after adding 0.5 g of the super absorbent polymer to 40 mL of 0.9% saline, followed by stirring at 350 rpm for 3 minutes using a surface tension meter.

Hereinafter, the present invention will be described in more detail with reference to examples. However, these examples are for illustrative purposes only, and the invention is not intended to be limited by these examples.

EXAMPLES—PREPARATION OF SUPER ABSORBENT POLYMER COMPOSITION

Example 1

Step 1

100 g (1.388 mol) of acrylic acid, 0.26 g of polyethylene glycol diacrylate (Mn=508) as an internal cross-linking agent, 0.008 g of diphenyl (2,4,6-trimethylbenzoyl)phosphine oxide as a photopolymerization initiator, 0.2 g of sodium persulfate as a thermal polymerization initiator and 123.5 g of a 32% caustic soda solution were mixed in a 3 L glass container equipped with a stirrer and a thermometer at room temperature to prepare a monomer composition (degree of neutralization of acrylic acid: 70 mol %, solid content: 45 wt %).

Thereafter, the monomer composition was supplied at 500 to 2000 mL/min on a conveyor belt in which a belt having a width of 10 cm and a length of 2 m rotates at a speed of 50 cm/min. And, at the same time as the monomer composition was supplied, ultraviolet rays having an intensity of 10 mW/cm² were irradiated to perform a polymerization reaction for 60 seconds, thereby obtaining a hydrogel polymer having a moisture content of 55 wt %.

Step 2

Subsequently, sodium stearoyl-2-lactylate (Almax-6900, manufactured by Ilshinwells, melting point: 48-51° C.) represented by the following Chemical Formula 1-6 was added to the hydrogel polymer obtained by the above polymerization reaction in the form of an aqueous solution in hot water such that the content was 0.3 parts by weight based on 100 parts by weight of the hydrogel polymer. Then, the mixture was pulverized into particles having a particle diameter of 150 μm to 850 μm using a meat chopper. At this time, the used meat chopper includes a chopping module including a plurality of perforated plates, and each perforated plate has a plurality of fine chopping holes, so that the hydrogel polymer is discharged in a chopped form through the plurality of fine chopping holes. Specifically, the prepared hydrogel polymer first passed through a perforated plate having a hole size of 2 mm, and then secondly passed through a perforated plate having a hole size of 0.5 mm to be pulverized to a normal particle size. Herein, a moisture content of the hydrous super absorbent polymer particles contained in the pulverized product was 55 wt %.

[Chemical Formula 1-6]

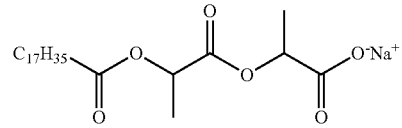

Step 3

Thereafter, a mixed solution for surface cross-linking containing 4.5 g of ultrapure water, 0.1 g of propylene glycol and 0.4 g of ethylene carbonate as a surface cross-linking agent was added to 200 g of the pulverized product, followed by mixing for 1 minute. Subsequently, the mixture was put into a paddle dryer capable of moving-type drying, and then kneaded at an internal temperature of 185° C. for 60 minutes to perform drying and surface cross-linking. After completion of the reaction, a super absorbent polymer composition was obtained without an additional pulverization process.

Example 2

A super absorbent polymer composition was prepared in the same manner as in Example 1, except that 0.15 g of polyethylene glycol diacrylate was used as an internal cross-linking agent.

Example 3

A super absorbent polymer composition was prepared in the same manner as in Example 2, except that 0.5 g of ethylene carbonate was used in the mixed solution for surface cross-linking.

Example 4

A super absorbent polymer composition was prepared in the same manner as in Example 2, except that sodium $C_{14-18}$-2-Lactylate (Almax-6600, manufactured by Ilshinwells, melting point: 44-46° C.) was used instead of the sodium stearoyl-2-lactylate.

Example 5

A super absorbent polymer composition was prepared in the same manner as in Example 2, except that monolauryl maleate represented by the following Chemical Formula 1-1 was used instead of the sodium stearoyl-2-lactylate. Herein, the monolauryl maleate represented by the following Chemical Formula 1-1 was prepared by mixing maleic acid anhydride and 1-dodecanol in a molar ratio of 1:1, followed by reacting at 60° C. for 3 hours.

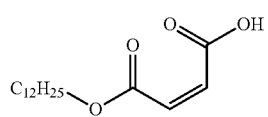

[Chemical Formula 1-1]

Comparative Example 1

(Polymerization) A hydrogel polymer having a moisture content of 55 wt % was obtained in the same manner as in Example 1.

(Chopping) Subsequently, the hydrogel polymer obtained by the polymerization reaction was mixed with the same amount of water as in Example 1, and chopped using a meat chopper having a perforated plate having a fine chopping hole size of 16 mm.

(Drying) Thereafter, a mixed solution for surface cross-linking containing 4.5 g of ultrapure water, 0.1 g of propylene glycol, and 0.4 g of ethylene carbonate was added to 200 g of the chopped hydrogel polymer, followed by mixing for 1 minute. Subsequently, drying and surface cross-linking were attempted to proceed after adding the mixture to a paddle dryer, but kneading could not proceed due to agglomeration between the hydrogel polymers.

Comparative Example 2

A super absorbent polymer composition was prepared in the same manner as in Example 1, except that polyethylene glycol (Mw=2000, manufactured by Miwon Specialty Chemical Co.) was used instead of the sodium stearoyl-2-lactylate represented by the Chemical Formula 1-6. However, the polymer was not discharged through the perforated plate due to excessive pressure generated inside the chopper, and the device was stopped.

Comparative Example 3

A super absorbent polymer composition was prepared in the same manner as in Example 1, except that sodium polyoxyethylene(3) lauryl ether carboxylate (LCA-30D, manufactured by Sanyo chemical) was used instead of the sodium stearoyl-2-lactylate represented by the Chemical Formula 1-6.

Comparative Example 4

(Polymerization) A hydrogel polymer having a moisture content of 55 wt % was obtained in the same manner as in Example 1.

(Chopping) Subsequently, the hydrogel polymer obtained by the polymerization reaction was mixed with the same amount of water as in Example 1, and chopped using a meat chopper having a perforated plate with a plurality of fine chopping holes having a hole size of 16 mm.

(Drying) Thereafter, the chopped hydrogel polymer was dried in an oven at 200° C. for 30 minutes in a fixed-bed type manner.

(Pulverization/Classification) The dried polymer was coarsely pulverized to a particle size of about 2 mm with a cutter mill (PULVERISETTE 19, manufactured by Fritsch), and then classified. Thereafter, particles larger than 850 μm among the classified particles were finely pulverized with a roll mill (66 F Gran-U-Lizer, manufactured by MPE), and classified into normal particles and fine particles.

(Surface cross-linking) Thereafter, a mixed solution for surface cross-linking containing 4.5 g of ultrapure water, 0.1 g of propylene glycol, and 0.4 g of ethylene carbonate was added to 200 g of the classified normal particles, followed by mixing for 1 minute. Subsequently, a surface cross-linking reaction was performed using a convection oven at 198° C. for 60 minutes. Then, it was classified to prepare a super absorbent polymer composition containing super absorbent polymer particles having a size of 150 to 850 μm.

Experimental Example 1

For the super absorbent polymer compositions prepared in Examples and Comparative Examples, centrifuge retention capacity (CRC) and absorbency under pressure (AUP) were measured in the following manner, and the results are shown in Table 1 below.

(1) Centrifuge Retention Capacity (CRC)

The centrifuge retention capacity by absorption ratio under a non-loading condition of each polymer composition was measured according to the EDANA (European Disposables and Nonwovens Association) WSP 241.3 method.

Specifically, a polymer composition was obtained by classifying each of the polymer compositions prepared in Examples and Comparative Examples through a sieve of #30-50. After inserting $W_0$ (g, about 0.2 g) of the polymer composition uniformly in a nonwoven fabric envelope and sealing the same, it was soaked in saline (0.9 wt %) at room temperature. After 30 minutes, the envelope was centrifuged at 250 G for 3 minutes to drain, and the weight $W_2$ (g) of the envelope was measured. Further, after carrying out the same operation without using the resin, the weight $W_1$ (g) of the envelope was measured.

Then, CRC (g/g) was calculated by using the obtained weight values according to the following Equation 1.

$$CRC\ (g/g) = \{[W_2(g) - W_1(g)]/W_0(g)\} - 1 \qquad \text{[Equation 1]}$$

(2) Absorbency Under Pressure (AUP)

The absorbency under pressure at 0.7 psi of the super absorbent polymer compositions prepared in Examples and Comparative Examples was measured according to the EDANA WSP 242.3 method.

First, in the measurement of the absorbency under pressure, the polymer in the above CRC measurement was used.

Subsequently, a glass filter was placed, and saline (0.9 wt % sodium chloride) was poured in the dish. At this time, the saline was poured until the surface level of the saline became equal to the upper surface of the glass filter. One sheet of filter paper with a diameter of 90 mm was placed thereon. After the measuring device was placed on the filter paper, the liquid was absorbed for 1 hour under a load. After 1 hour, the measuring device was lifted, and the weight $W_4$ (g) was measured.

Then, absorbency under pressure (g/g) was calculated by using the obtained weight values according to the following Equation 2.

$$AUP\ (g/g) = [W_4(g) - W_3(g)]/W_0(g) \qquad \text{[Equation 2]}$$

high surface tension and high bulk density while having water retention capacity and absorbency under pressure equal to or higher than the super absorbent polymer composition of Comparative Example 3 prepared by adding sodium polyoxyethylene(3) lauryl ether carboxylate before pulverizing the hydrogel polymer.

In addition, the super absorbent polymer compositions prepared according to Examples had the significantly reduced amount of fine powder generated, compared to the super absorbent polymer composition of Comparative Example 4 prepared according to the conventional process as shown in FIG. 1, in which chopping was performed without the use of additive, followed by drying, pulverization and classification, and then a separate surface cross-linking process.

Therefore, when the preparation of the super absorbent polymer is performed by adding the carboxylic acid-based additive during pulverization of the hydrogel polymer, and then simultaneously performing drying and surface cross-linking, pulverization to a normal particle size is possible without an additional pulverization process and the amount of fine powder generated is reduced, while preparing a super absorbent polymer with improved surface tension and bulk density.

TABLE 1

| | Additive | Normal particle content (wt %) | Amt. of fine powder generated (wt %) | SAP properties | | | |
|---|---|---|---|---|---|---|---|
| | | | | CRC (g/g) | AUP (g/g) | S/T (mN/m) | BD (g/ml) |
| Ex. 1 | Sodium stearoyl-2-lactylate | 91.1 | 2.9 | 28.3 | 20.2 | 72.3 | 0.69 |
| Ex. 2 | Sodium stearoyl-2-lactylate | 92.2 | 2.2 | 36.1 | 21.3 | 71.8 | 0.69 |
| Ex. 3 | Sodium stearoyl-2-lactylate | 92.0 | 2.3 | 34.9 | 23.8 | 71.7 | 0.69 |
| Ex. 4 | Sodium $C_{14-18}$-2-Lactylate | 91.9 | 2.4 | 35.9 | 21.6 | 72.1 | 0.69 |
| Ex. 5 | Monolauryl maleate | 91.9 | 2.3 | 36.0 | 21.5 | 71.6 | 0.69 |
| Comp. Ex. 1 | — | Not measurable | Not measurable | Not measurable | Not measurable | Not measurable | Not measurable |
| Comp. Ex. 2 | Polyethylene glycol | Not measurable | Not measurable | Not measurable | Not measurable | Not measurable | Not measurable |
| Comp. Ex. 3 | Sodium polyoxyethylene(3) lauryl ether carboxylate | 92.1 | 3.0 | 26.1 | 20.4 | 61.5 | 0.68 |
| Comp. Ex. 4 | — | 90.1 | 9.2 | 35.8 | 22.9 | 71.9 | 0.67 |

As shown in Table 1, it can be seen that Examples in which the carboxylic acid-based additive was added during pulverization of the hydrogel polymer to prepare a super absorbent polymer composition could simultaneously perform a drying process and a surface cross-linking process of the pulverized product after pulverizing the hydrogel polymer, unlike Comparative Example 1 in which the additive was not used and Comparative Example 2 in which polyethylene glycol was used.

In particular, when the super absorbent polymer composition was prepared in Examples, an additional pulverization process was not performed after the drying and surface cross-linking process, so the normal particle content finally measured in Examples can be considered to be the same as the normal particle content in the pulverized product prepared in (Step 2). Therefore, it is confirmed that the hydrogel polymer can be pulverized to a normal particle size, unlike the preparation methods of the super absorbent polymer composition of Comparative Examples 1 and 2.

In addition, it can be seen that the super absorbent polymer compositions prepared according to Examples had

What is claimed is:

1. A method of preparing a super absorbent polymer composition, comprising
    forming a hydrogel polymer by cross-linking polymerization of a water-soluble ethylene-based unsaturated monomer having at least partially neutralized acidic groups in the presence of an internal cross-linking agent and a polymerization initiator;
    mixing the hydrogel polymer with a carboxylic acid-based additive, followed by pulverization to prepare a pulverized product containing hydrous super absorbent polymer particles and the carboxylic acid-based additive; and
    mixing a surface cross-linking agent with the pulverized product followed by drying to prepare a super absorbent polymer composition containing; super absorbent polymer particles having a surface cross-linked layer formed on at least a part of a surface of the super absorbent polymer particles; and the carboxylic acid-based additive;
    wherein the carboxylic acid-based additive comprises at least one selected from the group consisting of a carboxylic acid represented by the following Chemical Formula 1 and a salt thereof:

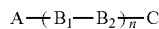
[Chemical Formula 1]

in Chemical Formula 1,
A is alkyl having 5 to 21 carbon atoms,
$B_1$ is —OCO—, —COO—, or —COOCH($R_1$)COO—,
$B_2$ is —$CH_2$—, —$CH_2CH_2$—, —CH($R_2$)—, —CH=CH—, or —C≡C—,
wherein, $R_1$ and $R_2$ are each independently alkyl having 1 to 4 carbon atoms,
n is an integer of 1 to 3, and
C is a carboxyl group.

2. The method of claim 1,
wherein the hydrogel polymer has a moisture content of 30 wt % to 70 wt %.

3. The preparation-method of claim 1,
wherein in Chemical Formula 1,
A is —$C_6H_{13}$, —$C_{11}H_{23}$, —$C_{12}H_{25}$, —$C_{17}H_{35}$, or —$C_{18}H_{37}$.

4. The method of claim 1,
wherein in Chemical Formula 1,
$B_1$ is

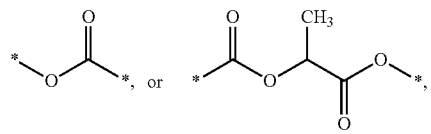

wherein * is a bonding site with a neighboring atom.

5. The method of claim 1,
wherein in Chemical Formula 1,
$B_2$ is

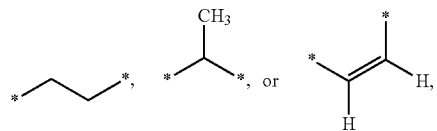

wherein * is a bonding site with a neighboring atom.

6. The method of claim 1,
wherein the carboxylic acid-based additive comprises at least one selected from the group consisting of a carboxylic acid represented by the Chemical Formula 1, an alkali metal salt thereof, and an alkaline earth metal salt thereof.

7. The method of claim 1,
wherein the carboxylic acid-based additive comprises any one of compounds represented by the following Chemical Formulae 1-1 to 1-7:

1-1
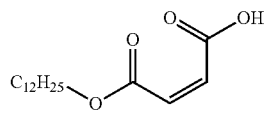

1-2
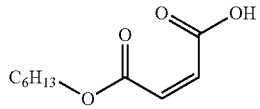

1-3
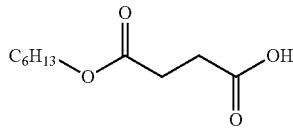

1-4
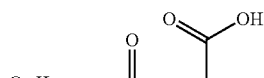

1-5
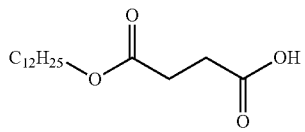

1-6
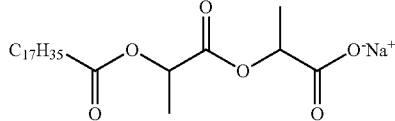

1-7
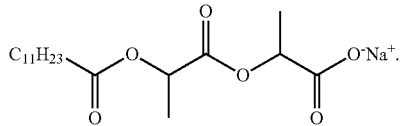

8. The method of claim 1,
wherein, in the mixing, an amount of the carboxylic acid-based additive mixed with the hydrogel polymer is 0.01 to 10 parts by weight based on 100 parts by weight of the hydrogel polymer.

9. The method of claim 1,
wherein the carboxylic acid-based additive is mixed in a solution form.

10. The method of claim 1,
wherein the pulverization is performed by a meat chopper.

11. The method of claim 10,
wherein the meat chopper comprises two or more perforated plates, and
each of the two or more perforated plates has a plurality of fine chopping holes having a certain size.

12. The method of claim 11,
wherein the meat chopper comprises a first perforated plate and a second perforated plate,
a hole size of the fine chopping holes provided in the first perforated plate is 1.5 mm to 5 mm, and
a hole size of the fine chopping holes provided in the second perforated plate is 0.2 mm to 1.2 mm.

13. The method of claim 1,
wherein the hydrous super absorbent polymer particles have a moisture content of 30 wt % to 70 wt %.

14. The method of claim 1,
wherein the pulverized product contains 90 wt % or more of hydrous super absorbent polymer particles having a particle diameter of 150 μm to 850 μm based on a total weight of pulverized product.

15. The method of claim 1,
at least some of the carboxylic acid-based additive in the pulverized product is present on a surface of the hydrous super absorbent polymer particles.

16. The method of claim 1,
wherein an amount of the surface cross-linking agent is 0.001 to 5 parts by weight based on 100 parts by weight of the pulverized product.

17. The method of claim 1,
wherein the drying is performed in a moving type manner.

18. The method of claim 1,
wherein the drying is performed at a temperature of 80° C. to 250° C. for 10 minutes to 3 hours.

19. The method of claim 1,
wherein the super absorbent polymer composition contains less than 10 wt % of fine powder having a particle diameter of less than 150 μm based on the total weight.

20. The method of claim 1,
wherein the method which does not comprise an additional pulverization step-after the drying the pulverized product.

\* \* \* \* \*